United States Patent

El-Chahawi et al.

[11] 4,228,097
[45] Oct. 14, 1980

[54] METHOD OF PREPARING α-HYDROXYMETHYLENE NITRILES

[75] Inventors: Moustafa El-Chahawi, Troisdorf; Uwe Prange, Niederkassel-Ranze, both of Fed. Rep. of Germany

[73] Assignee: Dynamit Nobel Aktiengesellschaft, Troisdorf, Fed. Rep. of Germany

[21] Appl. No.: 963,713

[22] Filed: Nov. 27, 1978

[30] Foreign Application Priority Data

Nov. 30, 1977 [DE] Fed. Rep. of Germany ....... 2753322

[51] Int. Cl.$^2$ ................. C07C 121/34; C07C 121/75; C07C 121/76
[52] U.S. Cl. ........................... 260/465 F; 260/465 D; 260/465 G; 260/465 H; 260/465 R; 260/465.1; 260/465.4; 260/465.6; 260/465.8 R; 546/330
[58] Field of Search ............ 260/465 R, 465.6, 465 F, 260/465.1, 465 D, 465 G, 465 H, 465.4, 465.8 R

[56] References Cited

U.S. PATENT DOCUMENTS

| | | | |
|---|---|---|---|
| 3,211,778 | 10/1965 | Kollonitsch | 260/465.6 |
| 3,742,017 | 6/1973 | Miyashiro et al. | 260/465.6 |

*Primary Examiner*—Dolph H. Torrence
*Attorney, Agent, or Firm*—Sprung, Felfe, Horn, Lynch & Kramer

[57] ABSTRACT

A method for the preparation of a compound of the formula

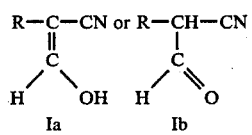

Ia    Ib or salt thereof bearing one or more α-hydroxymethylene groups, wherein the univalent moiety R is hydrogen, a straight chain or branched alkyl group of 1 to 20 carbon atoms, a straight chain or branched moiety of the formula,

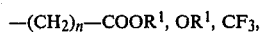

wherein n is from 0 to 5, a straight chain or branched moiety of the formula

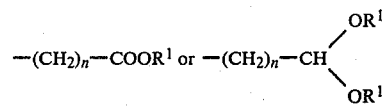

wherein each $R^1$ independently represents an alkyl radical of 1 to 12 carbon atoms, or a univalent phenol moiety and n has the meaning above, a substituted or unsubstituted moiety of the formula

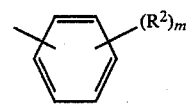

with m = 1 to 3 wherein $R^2$ is hydrogen, an alkyl group of 1 to 6 carbon atoms, a —(CH$_2$)$_n$—COOR$^1$, chlorine, bromine, —OR$^1$, CF$_3$, —(CH$_2$)$_n$—CN, where n and $R^1$ have the meanings given above, a ring system of the heterocyclic or isocyclic, monocyclic or polycyclic structure which comprises contacting a nitrile of the formula

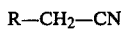

II wherein R has the meaning given above with carbon monoxide in the presence of an alcoholate and a solvent. Thereafter, the so formed salt can be separated or, if desired, the same can be converted into the free form of the compound Ia or Ib by acidification. Also disclosed are new α-hydroxymethylene and nitriles as well as their corresponding salts.

16 Claims, No Drawings

METHOD OF PREPARING α-HYDROXYMETHYLENE NITRILES

BACKGROUND OF THE INVENTION

1. Field of the Invention

This invention relates to a method for the preparation of α-hydroxymethylene nitriles and α-formyl nitriles or their tautomers of the formulae $$\underset{Ia}{R-\underset{\underset{H}{\diagup}\underset{OH}{\diagdown}}{\overset{\|}{C}}-CN} \quad \text{and} \quad \underset{Ib}{R-\underset{\underset{H}{\diagup}\underset{O}{\diagdown\!\!\!\diagdown}}{\overset{|}{C}}-CN}$$

as well as their corresponding alkali and alkaline earth metal salts especially salts of the formula Ia by reaction of the corresponding nitriles with carbon monoxide in the presence of an alcoholate. This invention is further directed to certain new and useful α-hydroxymethylene nitriles or α-formyl nitriles or their tautomeric mixtures or their salts or mixtures of their salts. This invention is particularly directed to a method for preparing such nitriles in an economically feasible manner whereby the nitriles are obtained in a relatively high yield.

2. Discussion of the Prior Art

The preparation of α-hydroxymethylene nitriles is difficult in the present state of the art.

A number of compounds of General Formulas Ia and Ib are formed, according to Ann. 512, 97–111 (1934) by the reaction of aliphatic nitriles with formic acid esters in the presence of alkali metals and alkali alcoholates, respectively. The yields, however, are low.

According to Bull. Soc. Chim. France, 1961, 1144–7, α-formyl-α-phenylacetonitrile can be isolated by the reaction of benzyl cyanide with formic acid ester in the presence of sodium alcoholate.

Unsatisfactory in these methods of preparation are the poor yields and the handling of formic acid esters, which are highly volatile and very toxic.

Other methods, such as the reaction of isoxazoles $$\underset{}{R^2}\underset{O}{\underset{\diagdown\!\!\!\diagdown}{\overset{\diagup\!\!\!\diagup}{N}}}$$

wherein $R^2$ represents $CH_3$ and phenyl, with alkali alcoholates (C.A. Vol. 50, 6432 (1956) and the preparation of cyanacetaldehyde from malonic aldehyde dioxim (German Ofenlegungsschrift No. 1,920,346) in several steps, are difficult and uneconomical.

By the hydroformylation of acrylonitrile with hydrogen and carbon monoxide (J. Chem. Soc. D, 1970, 1255) in the presence of $Co_2(CO)_8$, α-formylpropionitrile is obtained in a 7.8% yield. Aside from the pressures required in hydroformylations, β-isomers are formed preferentially. This method can be applied to only a very few compounds.

It is an object of the present invention to prepare α-hydroxymethylene nitriles and α-formyl nitriles in high yields and in an economical manner by a process that can be performed economically and commercially.

SUMMARY OF THE INVENTION

The foregoing objects are achieved in accordance with the present invention which provides a process for the preparation of an α-hydroxymethylene nitrile or an α-formyl nitrile or tautomer thereof of the formulae $$\underset{Ia}{R-\underset{\underset{H}{\diagup}\underset{OH}{\diagdown}}{\overset{\|}{C}}-CN} \quad \text{and} \quad \underset{Ib}{R-\underset{\underset{H}{\diagup}\underset{O}{\diagdown\!\!\!\diagdown}}{\overset{|}{C}}-CN}$$

as well as salts thereof especially salts of the first of said formulae, wherein the univalent moiety R represents:
a hydrogen atom,
a straight or branched alkyl moiety of 1 to 20 carbon atoms,
a straight or branched moiety of the formula $-(CH_2)_n-CN$ where n has a value of 0 to 5,
a straight chain or branched moiety of formula $-(CH_2)_n-COOR^1$ or $-(CH_2)_n-CH_2(OR^1)_2$ wherein each $R^1$ individually respresents an alkyl radical of 1 to 12 carbon atoms or an univalent phenol and n has the meaning given above;
substituted or unsubstituted moiety of the formula <br>(benzene ring with $(R^2)_m$ substituent)

wherein m is 1 to 3
$R^2$ is a hydrogen atom, an alkyl group of 1 to 6 carbon atoms, a moiety of the formula $-(CH_2)_n-COOR^1$, chlorine, bromine, $OR^1$, $CF_3$, $-(CH_2)_n-CN$, where n and R have the meaning given above, or R represents a ring system of a heterocyclic or isocyclic, monocyclic or polycyclic structure which process comprises contacting a nitrile of the formula:

$$R-CH_2-CN \quad\quad\quad II$$

wherein R has the meaning given above, with carbon monoxide in the presence of an alcoholate.

The process of the present invention is generally carried out in the presence of a solvent. By such a process there is formed a salt which can be isolated and separated from the reaction mixture and, if desired, can be converted to a free compound of the formula Ia or Ib, as the case may be, by acidification by contacting the same with an aqueous acidic solution. Alternatively, the salt can be converted to the free compound whose formula is Ia or Ib by contacting same with the acid while the same remains in admixture with other components of the reaction product.

Generally, the process is carried out using a stoichiometric amount of alcohol based upon the number of active $-CH_2-CN$ groups in the nitrile reactant employed. Generally speaking, the alcoholate is present in an amount of between 1 and 1,5 moles alcoholate per active $-CH_2-CN$ group in the nitrile reactant preferably between 1 and 1,1 moles per $-CH_2-CN$ reactant.

The process is generally carried out in the presence of an alcohol. The alcohool can be an aliphatic alcohol especially a straight or branched alkanol. Particularly contemplated alcohols include aliphatic alcohols having 1 to 8 carbon atoms especially 1 to 4 carbon atoms. The alcohol can be one whose organo group corresponds with the organo group of the alcoholate employed. Stated differently, the alcoholate can be alcohol of the alcohol which is also present.

Generally speaking, the amount of moles of alcohol is between 0,1 and 10 moles per mole of nitrile reactant preferably between 0,1 and 5 moles.

The wide variety of different alcoholates can be employed.

Generally speaking, the process can be carried out in the presence of a solvent. The solvent can be a polar or non polar solvent. Particular types of solvents are set forth in the ensuing disclosure.

With respect to the reactant, if an additional substituent —$CH_2$—CN is present in the moiety R of the nitrile reactant, the products of the process have an additional α-hydroxymethylene nitrile on this substituent.

With regard to the alkyl radicals of the moieties R, those are preferred which have from one to four carbon atoms; of the ester moieties those are preferred in which $R^1$ represents alkyl groups of one to six, especially one to two carbon atoms; of the moieties

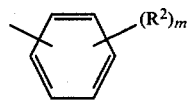

those are preferred which have one to three substituent $R^2$ representing H, o-alkyl, m-alkyl or p-alkyl with one to six, especially one or two carbon atoms, the moiety —$COOR^1$ with $R^1$ preferably having one or two carbon atoms, and in which $R^2$ represents —$(CH_2)_n$—CN with n=1; and of the heterocyclic and isocyclic ring systems, the monocyclic structures pyridyl, thionyl and furyl and the polycyclic structures α- and β-naphthyl are preferred.

One can employ substances having other substituents R, but some of them give rise to the formation of product mixtures or to secondary reactions, so that they are less desirable and therefore they have not been listed.

By the process of the invention one can prepare, for example, α-formylpropionitrile, α-formylbutyronitrile, α-formyl-γ-methylglutaric acid dinitrile, α-formylglutaric acid dinitrile, α-formyladipic acid dinitrile, α-formylcyanoacetic ester, α-formyl-α-phenylacetonitrile, o-, m-, p-methylphenyl-α-formylacetonitriles, α-formyltrifluoromethylphenylacetonitrile, o-, m-, p-chlorophenyl-α-formylacetonitriles, o-, m-, p-methoxyphenyl-α-formylacetonitriles, α-formyl-(p-phenylene)-diacetonitrile, α, α-diformyl-(p-phenylene)-diacetonitrile, α-formyl-(3-pyridyl)-acetonitrile, α-formyl-α-(1-naphthyl)-acetonitrile and α-formyl-α-(2-naphthyl)-acetonitrile and the corresponding tautomeric α-hydroxymethylene compounds and their salts.

If nitriles of General Formula II are used, wherein R represents —$(CH_2)_n$—CN with n=1–3, and wherein R represents

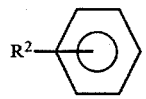

with $R^2$=—$(CH_2)_n$—CN and n=1 to 3, the corresponding α, α'-diformyl compounds can be prepared by using two moles of alcoholate per mole of dinitrile and, accordingly, two moles of carbon monoxide. If in substances of Formula II there are additional nitrile groups which are not bound to the group —$CH_2$—, for example the moiety

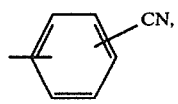

no formyl group occurs in this position.

When a plurality of nitrile groups are present, bis- or polyformyl nitriles will be formed, provided that one mole of alcoholate $M^I(OR)$ and one mole of CO are present for each mole of reactive groups —$CH_2$—CN, or, if desired, only one formyl group or less than the maximum possible number of formyl groups occurs, provided that the molar amount of alcoholate and/or, if desired, the molar amount of CO is limited to, for example, one equivalent, or else one —CN group has no adjacent methylene group.

Aliphatic alcohols having one to eight carbon atoms are used as the alcohol component of the alcoholates, alcohols having one to four carbon atoms being preferred, such as methanol, ethanol, propanol, isopropanol, n- or iso-butanol and tertiary butanol, and methanol and ethanol are greatly preferred. The alcohols can be those identified with the alkoxy groups of the alcoholates, or they can differ, if desired.

The amounts of the alcohols can be from 0.1 to 10 moles of alcohol per mole of starting substance.

The carbon monoxide can be used at pressures ranging from 5 to 100 bars. Higher pressures are possible, but are not necessary. Preferably the process is performed in the pressure range from 10 to 50 bars. The carbon monoxide can be contaminated with other gases such as nitrogen or hydrogen.

The temperature can be between 0° and 200° C., preferably 30° to 120° C. The reaction is slightly exothermic, but does not require additional cooling.

The reaction is performed preferably from 60 to 360 minutes, especially 60 to 120 minutes.

In general, the reaction is performed by placing the nitrile of General Formula II, the alcoholate, and the alcohol and solvent together under a nitrogen gas atmosphere in an autoclave provided with a stirrer. Then the required carbon monoxide pressure is established, and additional carbon monoxide is added to maintain the pressure until the end of the reaction. For the achievement of higher yields, it is desirable to operate in anhydrous or dried solvents.

Suitable solvents or dispersants are those which are inert with respect to the reaction components. Especially desirable are the aliphatic or cyclic ethers as diethyl ether or dimethoxyethane, dioxane or tetrahydrofuran, aliphatic or aromatic hydrocarbons such as the gasoline fraction called "petroleum ether," benzene, toluene or xylene and aprotic solvents such as dimethylformamide, dimethylsulfoxide or hexamethyl phosphoric acid triamide. Benzene and toluene are preferred. The total amount of the solvents is to be such as to assure a thorough mixing of the phases.

In a number of cases, the additional use of alcohols, especially methanol or ethanol, has proven beneficial. The amount is not to exceed 0.1 to 10 moles of alcohol per mole of nitrile.

After the end of the reaction, the salts of the hydroxymethylene nitriles can be obtained by filtration, evaporation of the solvents, or precipitation, for example. The cations of these salts correspond to those of the alcoholates used. The free compounds can be obtained from the salts or directly from the reaction mixture after acidification, preferably with a mineral acid, especially hydrochloric acid.

The conversion of the salt to the free product can be effected using an acid solution, especially an acidic aqueous solution. The acid of the solution can be any of the following acids: formic acid, acetic acid, phosphoric acid, hydrochloric acid or sulphuric acid.

Preferably the acid is a mineral acid. The acid is present in a normality of between 1 and 30 preferably between 4 and 12. The acidic solution is employed in at least a stoichiometric amount to remove the cation of the salt and to replace the same with hydrogen. For this reason mineral acids and active organic acids such as acetic acid are especially useful.

A number of aliphatic compounds of Formulas Ia and Ib are unstable.

Identification is performed, for example, as 2,4-dinitrophenylhydrazones or by spectroscopic methods.

The prepared substances of Formulas Ia and Ib can be employed either as the free compounds or as salts.

Whenever the free compounds of Formulas Ia or Ib are not very stable, their employment in the form of salts is preferred.

The substances of Formulas Ia and Ib and their salts are valuable chemical products for a wide variety of syntheses, including the preparation of derivatives of heterocyclic compounds which otherwise would be difficult to obtain by the formation of the ring together with bifunctional reactive compounds.

The substances of Formula Ia and Ib, which are much more simply obtainable by the present method, therefore permit the achievement of advances in the preparation of a great variety of secondary products.

Such secondary products include the pyrazole derivatives formed from hydrazine and α-phenyl- and α(p-chlorophenyl)-α-hydroxy-acrylonitrile (Ib) in accordance with U.S. Pat. No. 2,989,539, which are employed as muscle relaxants. In accordance with U.S. Pat. No. 3,828,091, α-aryl-β-hydroxyacrylonitrile (b) is reacted with thiols to form herbicides.

α-Phenyl-β-hydroxy-acrylonitrile (Ib) is used in accordance with German Pat. No. 1,019,220 as a catalyst for the polymerization of vinyl or vinylidene monomers.

Cyanacetaldehyde is used according to Japanese application 07 723 (1969) for the improvement of heat-resistant insulating paper.

Another direct application of the substances prepared is their employment as stabilizing agents for aliphatic chlorinated hydrocarbons.

In order to more fully illustrate the nature of the invention and in a manner of practising the same, the following examples are presented.

EXAMPLES

The following general instructions relate to the preparation of the sodium or potassium salts of the α-hydroxymethylene nitriles Ib.

One mole of nitrile of General Formula II (Examples 1-17, see Table 1), 1 mole of solid sodium or potassium alcoholate, 4 moles of the alcohol identified with the alkoxy group of the alcoholate, and 300 ml of benzene are placed together in a nitrogen gas atmosphere with the exclusion of moisture in a one-liter lift autoclave. Then, with stirring, a carbon monoxide pressure of 30 to 50 bars is established. The absorption of the carbon monoxide usually takes place immediately, the temperature of the reaction mixture increasing from about 25° to 35° C. In the case of some nitriles it is advantageous to increase the temperature to as much as 100° C. After about 4 to 5 hours the reaction has ended. The pressure in the autoclave is released and the reaction mixture is removed out of the autoclave. In the case of insoluble products, the solvent is removed by suction filtration and the product is dried in a vacuum of 20 to 50 Torr at about 50° C. In the case of soluble products, the solvent is distilled out in a vacuum of 20 to 50 Torr, and the product is then dried as described above.

TABLE 1

| Example | Educt | Alcoholate | Pressure | Temp. (°C.) | Product | Yield (%) |
|---|---|---|---|---|---|---|
| 1 | Acetonitrile | $NaOC_2H_5$ One mole | 30-50 | 50 | $NaO-CH=CH-CN$ | 90 |
| 2 | Acetonitrile | $KOC_2H_5$ One mole | 20-50 | 50 | $KO-CH=CH-CN$ | 92 |
| 3 | Acetonitrile | $KOCH_3$ One mole | 30-50 | 50 | $KO-CH=CH-CN$ | 86 |
| 4 | Propionitrile | $NaOC_2H_5$ One mole | 30-50 | 60 | $H_3C-C-CN$ $\parallel$ $H-C-ONa$ | 85 |
| 5 | Butyronitrile | $NaOC_2H_5$ One mole | 30-50 | 50-60 | $H_3C-CH_2-C-CN$ $\parallel$ $H-C-ONa$ | 80 |
| 6 | 2-Methylglutaric acid dinitrile | $NaOC_2H_5$ One mole | 30-50 | 50 | $NC-CH-CH_2-C-CN$, $CH_3$, $\overset{C}{\underset{H\diagup \diagdown ONa}{\parallel}}$ | 89 |
| 7 | Adipic acid dinitrile | $NaOC_2H_5$ One mole | 30-50 | 60 | $NC-CH_2-CH_2-CH_2-C-CN$ $\parallel$ $H-C-ONa$ | 82 |
| 8 | Cyanoacetic acid ethyl ester | $NaOC_2H_5$ One mole | 35-60 | 100 | $\underset{H}{\overset{NaO}{\diagdown}}C=C\underset{COOC_2H_5}{\overset{CN}{\diagup}}$ | 79 |

TABLE 1-continued

| Example | Educt | Alcoholate | Pressure | Temp. (°C.) | Product | Yield (%) |
|---|---|---|---|---|---|---|
| 9 | Phenylacetonitrile | NaOC$_2$H$_5$ | 40 | 40-45 | 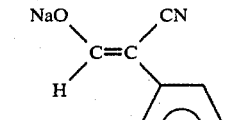 | 92 |
| 10 | p-Chlorophenyl acetonitrile | NaOC$_2$H$_5$ | 40 | 40-45 | 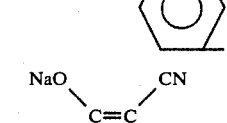 | 85 |
| 11 | p-Methylphenyl acetonitrile | NaOC$_2$H$_5$ | 40 | 40-45 | 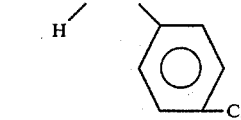 | 90 |
| 12 | m-Methylphenyl acetonitrile | NaOC$_2$H$_5$ | 40 | 40-45 | 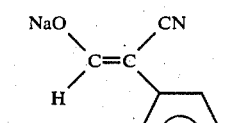 | 88 |
| 13 | o-Methylphenyl acetonitrile | NaOC$_2$H$_5$ | 40 | 45 | 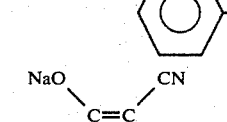 | 85 |
| 14 | p-Phenylene diacetonitrile | NaOC$_2$H$_5$ One mole | 50 | 40 | 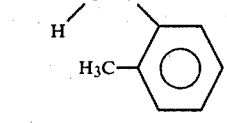 | 80 |
| 15 | p-Phenylene diacetonitrile | NaOC$_2$H$_5$ Two moles | 100 | 60 | 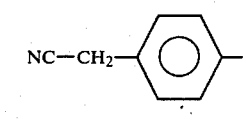 | 93 |
| 16 | 1-Naphthylacetonitrile | NaOC$_2$H$_5$ | 50 | 50 | 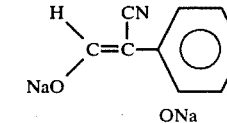 | 89 |
| 17 | 2-Naphthylacetonitrile | NaOC$_2$H$_5$ | 50 | 50 | 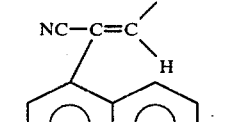 | 92 |
| 18 | 3-Pyridylacetonitrile | NaOC$_2$H$_5$ | 50 | 50 | 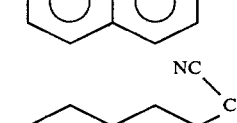 | 92 |
| 19 | p-Methoxyphenylacetonitrile | NaOC$_2$H$_5$ | 50 | 50 | 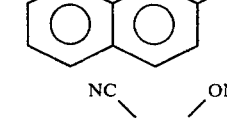 | 91 |

TABLE 1-continued

| Example | Educt | Alcoholate | Pressure | Temp. (°C.) | Product | Yield (%) |
|---|---|---|---|---|---|---|
| 20 | m-Methoxy-phenylacetonitrile | NaOC$_2$H$_5$ | 50 | 50 | 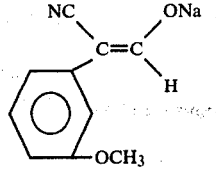 | 90 |
| 21 | m-Trifluoro-methylphenyl-acetonitrile | NaOC$_2$H$_5$ | 50 | 50 | 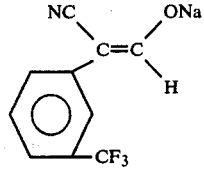 | 92 |

EXAMPLE 22

Preparation of α-formyl phenylacetonitrile

One mole of the salt prepared in Example 9 is treated with excess aqueous hydrochloric acid with vigorous stirring. α-Formyl-phenyl-acetonitrile precipitates in free form and is then removed by filtration and dried. The product is pure enough for additional reactions and has a melting point of 157°–158° C. After recrystallization from benzene, the melting point is 158°–160° C. The yield is 94% with respect to the salt charged.

EXAMPLES 23 to 34

By the method described in Example 22, the following α-formylnitriles were prepared from the salts of Examples 10 to 21, α,α'-bisformylnitriles being defined with the aid of the formula

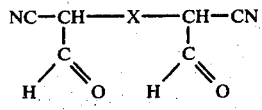

or tautomers thereof

|  |  |  | Yield (%) | m.p. °C. (uncorr.) |
|---|---|---|---|---|
| 23) | R = 4-chlorophenyl | (cf. Ex. 10) | 93 | 162–164 |
| 24) | R = 4-methylphenyl | (cf. Ex. 11) | 93 | 151–153 |
| 25) | R = 3-methylphenyl | (cf. Ex. 12) | 88 | 115–117 |
| 26) | R = 2-methylphenyl | (cf. Ex. 13) | 70 | 69–71 |
| 27) | R = p-acetonitrile-phenyl | (cf. Ex. 14) | 63 | 157–159 |
| 28) | X = phenylene | (cf. Ex. 15) | 78 | 224–225 |
| 29) | R = 1-naphthyl | (cf. Ex. 16) | 53 | 113–135 |
| 30) | R = 2-naphthyl | (cf. Ex. 17) | 85 | 181–182 |
| 31) | R = 3-pyridyl | (cf. Ex. 18) | 82 | 221–222 |
| 32) | R = p-methoxyphenyl | (cf. Ex. 19) | 86 | 117–118 |
| 33) | R = m-methoxyphenyl | (cf. Ex. 20) | 91 | 101–102 |
| 34) | R = m-trifluoromethyl | (cf. Ex. 21) | 72 | 98–101 |

Refer to the formulae Ia and Ib.

The compounds not known from the literature was identified on the basis of their molecular weights as determined by mass spectrometry and on the basis of their infrared and NMR spectra:

Substance of Example 26:
Mol. wt.: 159, theory: 159
Infrared spectrum: (in KBr)
  3150 cm$^{-1}$ OH (enol)
  2205 cm$^{-1}$ CN
  1635 cm$^{-1}$ C=C (enol)

NMR spectrum: in CDCl$_3$:
  δ=7.55 ppm broad singlet (OH) (1H)
  δ=7.33–7.1 ppm multiplet (5H)
  δ–2.33 ppm doublet (3H) 4.5 Hz Substance of Example 27:
Mol. wt.: 184 (mass spectrometry), theory: 184
Infrared spectrum: (in Kbr)
  3120 cm$^{-1}$, enol form: OH
  2210 cm$^{-1}$ CN
  2260 cm$^{-1}$ CN
  1635 cm$^{-1}$ C=C Substance of Example 28:
Mol. wt: 212 (mass spectrometry), theory: 212
Infrared spectrum: (in KBr)
  3131 cm$^{-1}$, enol form: OH
  2215 cm$^{-1}$, CN
  1640 cm$^{-1}$, C=C
NMR spectrum in DMSO-D$_6$, multiplet between δ=7.37–8.0 ppm (6H) broad bands around δ=5.4 ppm (2H)

Substance of Example 34:
Mol. wt.: 213 (mass spectrometry), theory: 213
Infrared spectrum: (in KBr)
  3090 cm$^{-1}$, enol-OH
  2215 cm$^{-1}$, CN
  1640 cm$^{-1}$, C=C
NMR spectrum in CDCl$_3$: multiplet between δ=7.23 and 8.02 ppm

EXAMPLE 35

Approximately 5 grams of the salt obtained in Example 6 were acidified with dilute HCl and extracted with ether. After drying the ether extract over MgSO$_4$ the ether is distilled off.

Infrared spectrum: (in substance)
  3200 cm$^{-1}$ OH (enol)
  2215 cm$^{-1}$ CN
  2205 cm$^{-1}$ CN
  1725 cm$^{-1}$ C=O (aldehyde)
  1655 cm$^{-1}$ C=C (enol)

Corresponding to the above-mentioned tautomers, both the aldehyde bands corresponding to the formyl group and the bands pertaining to the enol form were found.

EXAMPLE 36

As in Example 35, the enol and the aldehyde were obtained from the salt obtained in Example 7.
Infrared Spectrum: (in substance)
  3250 cm$^{-1}$ OH (enol)

2720 cm$^{-1}$ C-H (aldehyde)
2220 cm$^{-1}$ CN
2200 cm$^{-1}$ CN
1745, 1730 cm$^{-1}$ C=C (aldehyde)
1655 cm$^{-1}$ C=C (enol)

What is claimed is:

1. A method for the preparation of a compound of the formula $$\underset{\text{Ia}}{\overset{\text{R-C-CN}}{\underset{\text{H}}{\overset{\parallel}{\underset{\diagdown}{\text{C}}}}\text{OH}}} \text{ or } \underset{\text{Ib}}{\overset{\text{R-CH-CN}}{\underset{\text{H}}{\overset{|}{\underset{\diagdown}{\text{C}}}}\text{O}}}$$

or salt thereof bearing one or more α-hydroxymethylene groups, wherein the univalent moiety R is hydrogen, a straight chain or branched alkyl group of 1 to 20 carbon atoms, a straight chain or branched moiety of the formula —(CH$_2$)$_n$ CN wherein n is from 0 to 5, a straight chain or branched moiety of the formula —(CH$_2$)$_n$—COOR$^1$ or —(CH$_2$)$_n$—CH$\underset{\text{OR}^1}{\overset{\text{OR}^1}{\diagup}}$ wherein each R$^1$ independently represents an alkyl radical of 1 to 12 carbon atoms, or a univalent phenol moiety and n has the meaning above, a substituted or unsubstituted moiety of the formula

[benzene ring]—(R$^2$)$_m$ with m = 1 to 3, wherein R$^2$ is hydrogen, an alkyl group of 1 to 6 carbon atoms, a —(CH$_2$)$_n$—COOR$^1$, chlorine, bromine, or —OR$^1$, CF$_3$, —(CH$_2$)$_n$—CN, where n and R$^1$ have the meanings given above, which comprises contacting a nitrile of the formula

R—CH$_2$—CN        II wherein R has the meaning given above with carbon monoxide in the presence of an alcoholate and a solvent.

2. A process according to claim 1 wherein the salt so formed is separated from the reaction mixture.

3. A process according to claim 2 wherein the so formed salt is contacted with an acid to form a free compound of the formula $$\underset{\text{Ia}}{\overset{\text{R-C-CN}}{\underset{\text{H}}{\overset{\parallel}{\underset{\diagdown}{\text{C}}}}\text{OH}}} \text{ or } \underset{\text{Ib}}{\overset{\text{R-CH-CN}}{\underset{\text{H}}{\overset{|}{\underset{\diagdown}{\text{C}}}}\text{O}}}$$

4. A process according to claim 1, wherein the reaction mixture is treated with an acid whereby to form a free compound of the formula Ia or Ib and the same is then separated.

5. A process according to claim 1 wherein the alcoholate is an alkali metal or alkaline earth metal.

6. A process according to claim 1 wherein the alcoholate is employed in a stoichiometric amount with respect to the number of —CH$_2$—CN groups in the compound whose formula is R—CH$_2$—CN.

7. A process according to claim 1 wherein the reaction is carried out in the presence of an alcohol.

8. A process according to claim 7 wherein said alcohol is an aliphatic alcohol having 1 to 8 carbon atoms.

9. A process according to claim 8 wherein said aliphatic alcohol has 1 to 4 carbon atoms.

10. A process according to claim 8 wherein said alcoholate is an alcoholate of the alcohol which is present.

11. A process according to claim 1 wherein the reaction is carried out in the presence of a solvent and said solvent is an aliphatic or cyclic ether, a low boiling aliphatic or aromatic hydrocarbon or an aprotic solvent.

12. A process according to claim 7 wherein said process is carried out in the presence of a solvent, said alcohol is one having 1 to 8 carbon atoms and said alcohol is present in an amount between 0.1 and 10 moles of alcohol per mole of compound whose formula is R—CH$_2$—CN.

13. A process according to claim 1 wherein the carbon monoxide pressure is 5 to 100 bars.

14. A process according to claim 13 wherein the carbon monoxide pressure is 10 to 50 bars.

15. A process according to claim 1 wherein the temperature of the reaction mixture is 0° to 200° C.

16. A process according to claim 15 wherein the temperature of the reaction mixture is 30° to 120° C.

* * * * *